United States Patent [19]

Cheng

[11] 4,151,203

[45] Apr. 24, 1979

[54] PROCESS FOR THE PREPARATION OF P-NITROANILINE COMPOUNDS BY THE ALKALINE HYDROLYSIS OF MIXED ANILIDES

[75] Inventor: Dah-Chieh O. Cheng, Kingsport, Tenn.

[73] Assignee: Eastman Kodak Company, Rochester, N.Y.

[21] Appl. No.: 932,159

[22] Filed: Aug. 9, 1978

[51] Int. Cl.$^2$ ............................................. C07C 85/26
[52] U.S. Cl. .................................... 260/582; 260/575; 260/578; 260/701
[58] Field of Search ......................... 260/575, 582, 578

[56] References Cited

U.S. PATENT DOCUMENTS

| | | | |
|---|---|---|---|
| 2,128,699 | 8/1938 | Frye | 260/582 |
| 2,671,110 | 3/1954 | Zbornik et al. | 260/582 |
| 2,732,392 | 1/1956 | Hardy | 260/582 X |

OTHER PUBLICATIONS

Henderson et al., "J. Org. Chem.," vol. 42 (25), pp. 3989–3994, (1977).
Ayrey et al., "J. Chem. Soc. B," vol. 4, pp. 738–739, (1970).
Kuellertz et al., "Tetrahedron," vol. 32(6), pp. 759–761, (1976).
Vinnik et al., "Chem. Ab.," vol. 67, Ab. No. 21218a, (1967).
Medvetskaya et al., "Chem. Ab.," vol. 71, Ab. No. 129246e, (1969).
Vinnik et al., "Chem. Ab.," vol. 84, Ab. No. 179235q, (1976).

Primary Examiner—Winston A. Douglas
Assistant Examiner—John Doll
Attorney, Agent, or Firm—J. Frederick Thomsen; Daniel B. Reece, III

[57] ABSTRACT

Process for the preparation of certain substituted p-nitroaniline compounds essentially free of the corresponding o-nitroaniline compounds. The process comprises subjecting an alkanol solution of the anilides of such compounds to alkaline hydrolysis conditions, thereby effecting hydrolysis and precipitation of the p-nitroaniline compound essentially free of the undesired o-isomer. The compounds are intermediates useful in the preparation of azo pigments.

11 Claims, No Drawings

PROCESS FOR THE PREPARATION OF P-NITROANILINE COMPOUNDS BY THE ALKALINE HYDROLYSIS OF MIXED ANILIDES

This invention concerns an improved process for the preparation of p-nitroanilines, the benzene ring of which contains, in addition to the amino and nitro groups, two substitutents. More particularly, this invention concerns a one-step technique for providing such p-nitroanilides in an essentially pure form.

The process of my invention for preparing p-nitroaniline I in an essentially pure form comprises subjecting a lower alkanol solution of o-nitroacylanilide II and a lower carboxylic acid amide of I to alkaline hydrolysis conditions and separating insoluble I thus formed from the reaction medium, wherein I and II each is a compound or an isomeric pair of compounds when X and Y are different having the formula

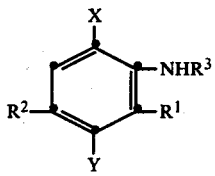

wherein X is halogen, lower alkyl, or lower alkoxy; Y is lower alkyl or halogen; and $R^1$, $R^2$ and $R^3$ are:

I: $R^1$ and $R^3$ each is hydrogen and $R^2$ is nitro; and
II: $R^1$ is nitro, $R^2$ is hydrogen and $R^3$ is lower carboxylic acid acyl.

The synthesis of compounds II and amides of compounds I beginning with a X,Y-substituted benzene involves nitrating the benzene compound, hydrogenating the product to obtain the corresponding aniline compound which, after acylating the amino group, is then nitrated again. This reaction sequence is:

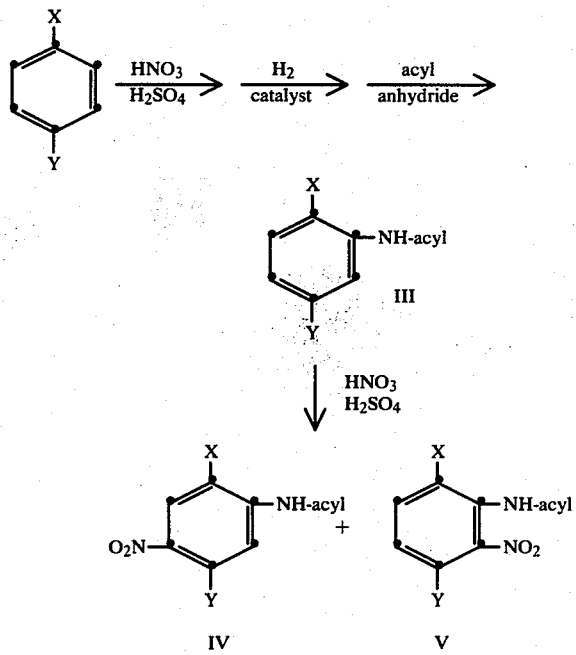

As is shown, the second nitration results in nitration of the aromatic nucleus, with respect to the acylamide group, not only at the desired para position but also at the ortho position. When X and Y are different substituents, such as in the case of p-chlorotoluene, formulas III, IV and V each represents an isomeric pair of compounds, i.e., X=Cl, Y=CH₃ and X=CH₃, Y=Cl.

The p-nitroaniline compounds I derived from p-nitroanilides of formula IV are intermediates useful in the preparation of azo pigments. For example, the p-nitroaniline can be hydrogenated to the corresponding diamine which is then reacted with diketene to form a 1,4-bis(acetoacetamido)-2,5-X,Y-benzene. The last-mentioned compound can be employed as a coupling component in the synthesis of pigments, for example, by coupling with a diazotized aromatic amine to give a yellow pigment. The manufacture and use of these types of pigments are described German OLS Nos. 2,243,955, 2,244,035, 2,254,625, 2,312,734 and 2,326,298.

It is known that the quality and performance of pigments must be consistent and dependable and therefore the materials used in pigment production must not contain impurities which affect the properties of the pigment such as hue, color density and fastness properties. The use of compounds I as intermediates would not be desirable or feasible if such compounds contained significant quantities of the corresponding o-nitroaniline compound. If a mixture of the compounds of formulas IV and V is subjected to acid hydrolysis conditions, both isomers are hydrolyzed to the corresponding nitroanilines. Separation of the p-nitroaniline from the o-nitroaniline has proved to be particularly difficult. For example, obtaining the desired compound in acceptable purity requires three or more recrystallizations from toluene.

I have discovered that if a mixture of compounds IV and V dissolved in an alcohol are subjected to alkaline hydrolysis conditions, IV is hydrolyzed to the p-nitroaniline compound and can be precipitated from solution whereas V is unaffected by the conditions and remains in solution. My novel process thus not only accomplishes the necessary hydrolysis of the amide to the amine but very conveniently and economically provides the desired p-nitroaniline in an essentially pure form, i.e., essentially free of the o-nitroaniline.

The alkaline hydrolysis conditions utilized in the practice of my novel process are well known and include the use of hydrolyzing-effective amounts of both water and a basic material such as the hydroxides of the alkali metals, for example, sodium and potassium. The use of sodium and potassium carbonate is not preferred since, in addition to hydrolyzing the p-nitroanilides, they cause precipitation of some of the o-nitroanilide. The amount of water employed can be widely varied provided there is at least a 1:1 stoichiometric ratio of water to the amide of I present. Generally the mol ratio of water to the amide of I will be in the range of about 2:1 to about 6:1 or more. The amount of basic material can be varied from about 1 to about 4 equivalents per equivalent of the amide of I. However, the use of 1 equivalent of basic material generally requires prolonged heating for completion of the hydrolysis whereas the use of amounts approaching 4 equivalents can render I soluble in the reaction medium and thus cause diminished yields. Preferably, potassium and/or sodium hydroxide are used in a ratio of about 1.5 to 2.5 moles per mole of the amide of I. Mol ratios of 1.8 to 2.0 are especially preferred. Usually the base employed is in the form of a concentrated aqueous solution such as, for example, a 50% solution (50 weight parts base and 50 weight parts water) and thus the amount of water employed is dependent on the amount of the aqueous base solution used.

The alkanols which can be used are the common saturated alkanols containing up to about 4 carbons such as methanol, ethanol, n-propanol, isopropanol, n-butanol and isobutanol. Methanol is preferred since it is the most economical. It is apparent that the minimum amount of alkanol which is required is that amount which will dissolve the mixture of II and the amide of I, i.e., the mixture of the anilides of formulas IV and V. The upper limit of the amount of alkanol is not critical to the practice of the invention. Amounts of 20 mol of alkanol per mole of the mixture of anilides has given satisfactory results. For practical reasons, mol ratios of alkanol to anilide mixture of about 5 to 15 are preferred.

The temperature can be varied from about 25° to 125° C., although at lower temperatures the rate of hydrolysis is relatively slow. The practical upper limit on the temperature will be dependent on the constituents of the reaction mixture, i.e., the alkanol or alkanols used and the relative amounts of alkanol and water. Most conveniently, the process is carried out at, or moderately below, e.g., 5°–10° C., the reflux temperature of the reaction mixture. Thus, the preferred temperature when methanol is used is about 60° to 70° C.

To insure maximum precipitation of I and to provide a workable mixture of solid I and the water-alkanol mixture, additional water is added to the mixture after I begins to precipitate. The amount of water added will be determined by practical considerations and is not critical. Generally, good results are achieved by adding about 50 to 200 volume percent based on the volume of the starting reaction mixture. Precipitation, of course, is maximized by cooling the reaction mixture, for example, to room (or ambient) temperature.

The above-described alkaline or based-catalyzed hydrolysis conditions, as has been mentioned previously, are conventional and thus are well known to organic chemists.

The carboxylic acid acyl residue of II and the amides of I, i.e., the anilides of formulas IV and V, can contain from 2 to 4 carbon atoms and include acetyl, propionyl, butyryl and isobutyryl. Because of the availability and cost of acetic anhydride, acetyl is the preferred acyl residue in which case the mixture of anilides used in my novel process consists of a p-nitroacetanilide and an o-nitroacetanilide. Chlorine, bromine, methyl, ethyl, propyl, n-butyl, isobutyl, methoxy, ethoxy, propoxy and butoxy are examples of the substituents represented by X and Y. Chlorine, methyl and methoxy are preferred substituents. The process of my invention is especially useful in preparing p-nitroaniline compounds wherein X and Y each is methyl; X and Y each is chloro; X is chloro and Y is methyl (or v.v.); or X is methyl and X is methoxy (or v.v.).

The solid I which is produced according to the invention can be separated by conventional means such as, for example, by filtering or by centrifuging. As mentioned hereinabove, the p-nitroaniline compounds obtained can be hydrogenated to form the corresponding 1,4-phenylenediamines which can then be reacted with diketene to give 1,4-bis(acetoacetamido)benzene compounds which are useful as couplers in the preparation of azo pigments.

The invention will be further illustrated by the following examples although it will be understood that these examples are included merely for purposes of illustration and are not intended to limit the scope of the invention.

EXAMPLE 1

A mixture of 5-chloro-2-methyl-4-nitroacetanilide, 2-chloro-5-methyl-4-nitroacetanilide, 6-chloro-2-methyl-2-nitroacetanilide and 3-chloro-6-methyl-2-nitroacetanilide (total anilide content of approximately 1.2 mol) was prepared from p-chlorotoluene by the consecutive steps of nitration, hydrogenation, acetylation and nitration. The water-wet mixture of anilides was refluxed (~70° C.) with stirring with 600 ml. methanol, and 120 ml. of a 50% sodium hydroxide solution (50 weight parts sodium hydroxide and 50 weight parts water). After refluxing for 30 minutes 850 ml. of hot water was added, the mixture was again refluxed for 15 minutes and then cooled to room temperature. The yellow precipitate was filtered off and washed twice with 600 ml. water. The water-wet product consisting of 5-chloro-2-methyl-4-nitroaniline and 2-chloro-5-methyl-4-nitroaniline was then hydrogenated to give 1,4-diamino-2-chloro-5-methylbenzene.

EXAMPLE 2

A mixture of 2,5-dichloro-4-nitroacetanilide and 3,6-dichloro-2-nitroacetanilide (total anilide content of 0.05 mol) was prepared by the nitration of 0.05 mol of 2,5-dichloroacetanilide. The water-wet mixture of anilides was dissolved in 20 ml. of methanol and 20 ml. of a solution consisting of 88 g. potassium hydroxide, 63 ml. water and sufficient methanol to a total volume of 250 ml. The solution was refluxed on a steam bath for 15 minutes, diluted with 50 ml. hot water and heated an additional 15 minutes. After cooling to room temperature the product was filtered and dried to give 8.8 g. product, NMR analysis indicated the product was pure 2,5-dichloro-4-nitroaniline.

EXAMPLE 3

A mixture of the anilide isomers (0.2 mol), prepared as described in Example 1, in 100 ml. of methanol and 20 ml. of 50% aqueous sodium hydroxide was refluxed for 20 minutes, an additional 140 ml. of hot water was added and the mixture refluxed another 15 minutes. After cooling, the product was washed with water, filtered and dried to give 26.2 g. of essentially pure 5-chloro-2-methyl-4-nitroaniline and 2-chloro-5-methyl-4-nitroaniline. Acidification of the filtrate gave 10.3 g. of the corresponding 2-nitroacetanilide compounds.

EXAMPLE 4

A mixture of 2,5-dimethyl-4-nitroacetanilide and 3,6-dimethyl-2-nitroacetanilide was prepared by the nitration of 0.2 mol of 2,5-dimethylacetanilide. A solution of a portion of the water-wet mixture (total weight of 19 g.) in 40 mol methanol was refluxed for 15 minutes with 50% sodium hydroxide solution. To the reaction mixture was added 50 ml. of hot water followed by refluxing. Upon cooling 7.5 g. of 2,5-dimethyl-4-nitroaniline was recovered. Using essentially the same procedure but substituting isopropanol for the methanol, a second 19 g. portion of the acetanilide mixture gave 5 g. of 2,5-dimethyl-4-nitroaniline.

EXAMPLE 5

A mixture of 2-methoxy-5-methyl-4-nitroacetanilide and 3-methyl-6-methoxy-2-nitroacetanilide (prepared by nitrating 0.1 mol of 2-methoxy-5-methylacetanilide)

was dissolved in 30 ml. methanol and 10 ml. of 50% sodium hydroxide solution. The solution was refluxed for 15 minutes, 50 ml. of hot water was added and stirring was continued for 15 minutes. The reaction mixture was cooled to room temperature, the precipitate filtered off and washed with water to give 17 g. of 2-methoxy-5-methyl-4-nitroaniline. NMR analysis indicated that the product was free of the isomeric 2-nitroaniline compound.

The invention has been described in detail with particular reference to certain preferred embodiments thereof, but it will be understood that variations and modifications can be effected within the spirit and scope of the invention.

I claim:

1. Process for preparing I in an essentially pure form which comprises subjecting a lower alkanol solution of II and a lower carboxylic acid amide of I to hydrolysis conditions in the presence of sodium or potassium hydroxide and separating insoluble I thus formed from the reaction mixture, wherein I and II each is a compound or, when X and Y are different, an isomeric pair of compounds, having the formula

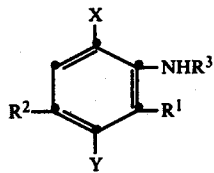

wherein X is halogen, lower alkyl or lower alkoxy; Y is halogen or lower alkyl; and $R^1$, $R^2$ and $R^3$ in the compounds or isomeric mixtures I and II are:

I: $R^1$ and $R^3$ hydrogen and $R^2$ is nitro; and
II: $R^1$ is nitro, $R^2$ is hydrogen, and $R^3$ is lower carboxylic acid acyl.

2. Process according to claim 1 which comprises heating a lower alkanol solution of II and an amide of I in the presence of water and a hydrolyzing effective amount of sodium hydroxide or potassium hydroxide.

3. Process of claim 2 wherein X is chloro, methyl or methoxy and Y is chloro or methyl.

4. Process for preparing I in an essentially pure form which comprises heating a methanol solution of II and the acetamide of I in the presence of a hydrolyzing-effective amount of water and sodium hydroxide or potassium hydroxide and separating insoluble I thus formed from the reaction medium, wherein I and II each is a compound or, when X and Y are different, an isomeric pair of compounds, having the formula

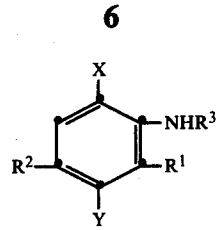

wherein X is chloro, methyl or methoxy; y is chloro or methyl; and $R^1$, $R^2$ and $R^3$ in the compounds or isomeric mixtures I and II are:

I: $R^1$ and $R^3$ are hydrogen and $R^2$ is nitro; and
II: $R^1$ is nitro, $R^2$ is hydrogen, and $R^3$ is acetyl.

5. Process according to claim 4 wherein the hydrolyzing-effective amount of sodium hydroxide or potassium hydroxide is from about 1.5 to 2.5 mol per mol of the acetamide of I.

6. Process according to claim 5 wherein I is 2,5-dichloro-4-nitroaniline and II is 3,6-dichloro-2-nitroacetanilide.

7. Process according to claim 5 wherein I is the isomeric pair 5-chloro-2-methyl-4-nitroaniline and 2-chloro-5-methyl-4-nitroaniline and II is the isomeric pair 6-chloro-3-methyl-2-nitroacetanilide and 3-chloro-6-methyl-2-nitroacetanilide.

8. Process for preparing I in an essentially pure form which comprises heating at a temperature of about 60° to 70° C. a methanol solution of II and the acetamide of I in the presence of about 1.8 to 2.0 mol of sodium hydroxide or potassium hydroxide per mol of the acetamide of I and a hydrolyzing-effective amount of water, adding a second portion of water to complete precipitation of I and separating I from the reaction medium, wherein I and II each is a compound or, when X and Y are different, an isomeric pair of compounds, having the formula

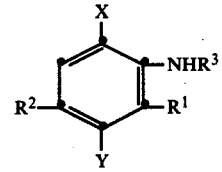

wherein X is chloro, methyl or methoxy; Y is chloro or methyl; and $R^1$, $R^2$ and $R^3$ in the compounds or isomeric mixtures I and II are:

I: $R^1$ and $R^3$ are hydrogen and $R^2$ is nitro; and
II: $R^1$ is nitro, $R^2$ is hydrogen, and $R^3$ is acetyl.

9. Process according to claim 8 wherein the mol ratio of alkanol to the total of mols of II and the amide of I is about 5 to 15.

10. Process according to claim 9 wherein I is 2,5-dichloro-4-nitroaniline and II is 3,6-dichloro-2-nitroacetanilide.

11. Process according to claim 9 wherein I is the isomeric pair 5-chloro-2-methyl-4-nitroaniline and 2-chloro-5-methyl-4-nitroaniline and II is the isomeric pair 6-chloro-3-methyl-2-nitroacetanilide and 3-chloro-6-methyl-2-nitroacetanilide.

* * * * *